(12) United States Patent
Stogniew et al.

(10) Patent No.: US 7,629,333 B2
(45) Date of Patent: *Dec. 8, 2009

(54) STABLE AMORPHOUS AMIFOSTINE COMPOSITIONS AND METHODS FOR THE PREPARATION AND USE OF SAME

(75) Inventors: Martin Stogniew, Blue Bell, PA (US); Javad M. Zadei, West Chester, PA (US)

(73) Assignee: MedImmune, LLC, Gaithersburg, MD (US)

( * ) Notice: Subject to any disclaimer, the term of this patent is extended or adjusted under 35 U.S.C. 154(b) by 713 days.

This patent is subject to a terminal disclaimer.

(21) Appl. No.: 11/017,190

(22) Filed: Dec. 21, 2004

(65) Prior Publication Data

US 2005/0209200 A1    Sep. 22, 2005

(51) Int. Cl.
*A61K 31/47*    (2006.01)
*A61K 31/66*    (2006.01)
*C07F 9/02*    (2006.01)
*A61P 39/00*    (2006.01)

(52) U.S. Cl. .......................... 514/143; 558/71; 558/146

(58) Field of Classification Search ................. 514/143; 558/71, 146
See application file for complete search history.

(56) References Cited

U.S. PATENT DOCUMENTS

| 3,892,824 | A |   | 7/1975 | Piper et al. ................... 260/944 |
| 4,424,216 | A |   | 1/1984 | Cerami et al. ................ 424/211 |
| 5,424,471 | A |   | 6/1995 | Kennedy et al. ............. 558/146 |
| 5,488,042 | A |   | 1/1996 | Grdina ........................ 235/103 |
| 5,591,731 | A | * | 1/1997 | Kennedy et al. ............. 514/114 |
| 6,384,259 | B1 | * | 5/2002 | Stogniew et al. ............ 558/146 |
| 6,407,278 | B2 | * | 6/2002 | Stogniew et al. ............ 558/146 |

FOREIGN PATENT DOCUMENTS

| JP | 54-46722 | 4/1979 |
| WO | WO 89/05637 | 6/1989 |
| WO | WO 95/07700 | 3/1995 |
| WO | WO 97/11666 | 4/1997 |
| WO | WO98/34622 | 8/1998 |

OTHER PUBLICATIONS

Bohuslavizki et al., "Protection of salivary glands by amifostine in patients treated with high dose radioiodine", Eu. Jour. Cancer 33: S17 (1997).
Fitchner et al., "Effects of amifostine on tumor growth and pharmacology of cytotoxic drugs in human xenotransplanted neuroblastomas", Anti-cancer Drugs 8(2): 174-181 (1997).
Foster-Nora et al., "Amifostine for protection from antineoplastic drug toxicity", Am. Jour. Health-system Pharm. 54(7): 787-800 (1997).
Jahansouz, H. et al. "Stability of ethiofos (NSC-29691) in aqueous solution and solid phase formulation" *Pharm. Res.* (NY) 7(9):S195 (1990).
Kemp et al., "Amifostine pretreatment for protection against cyclophosphatide-induced and cisplastin-induced toxicities: results of a randomized control trial in patients with advanced ovarian cancer", Jour. Clin. Oncology 14(7): 2101-2112 (1996).
Lewis, "A review of the use of chemoprotectants in cancer chemotherapy", Drug Safety: An International Journal of Medical Toxicology and Drug Experience 11(3): 153-162 (1994).
Spencer et al., "Amifostine. A review of its pharmacodynamic and pharmacokinetic properties, and therapeutic potential as a radioprotector and cytotoxic chemoprotector", Drugs 50(6): 1001-1031 (1995).
Zadeii et al., "Stability of Ethiofos (NSC-29691) in aqueous solution and solid phase formulation" *Pharm. Res.* (NY) 8(10 Suppl.):S174 (1991).

* cited by examiner

*Primary Examiner*—James O Wilson
*Assistant Examiner*—Tamthom N Truong
(74) *Attorney, Agent, or Firm*—Jones Day

(57) ABSTRACT

The present invention relates to a sterile, stable dosage forms suitable for reconstitution and parenteral administration to a patient, said dosage form comprising an amorphous aminoalkyl dihydrogen phosphorothioate, and of amifostine in particular. The invention further relates to a method of preparing such a dosage form, which typically exhibits enhanced thermal stability as compared to existing vacuum dried amorphous amifostine.

11 Claims, 4 Drawing Sheets

Figure 1:
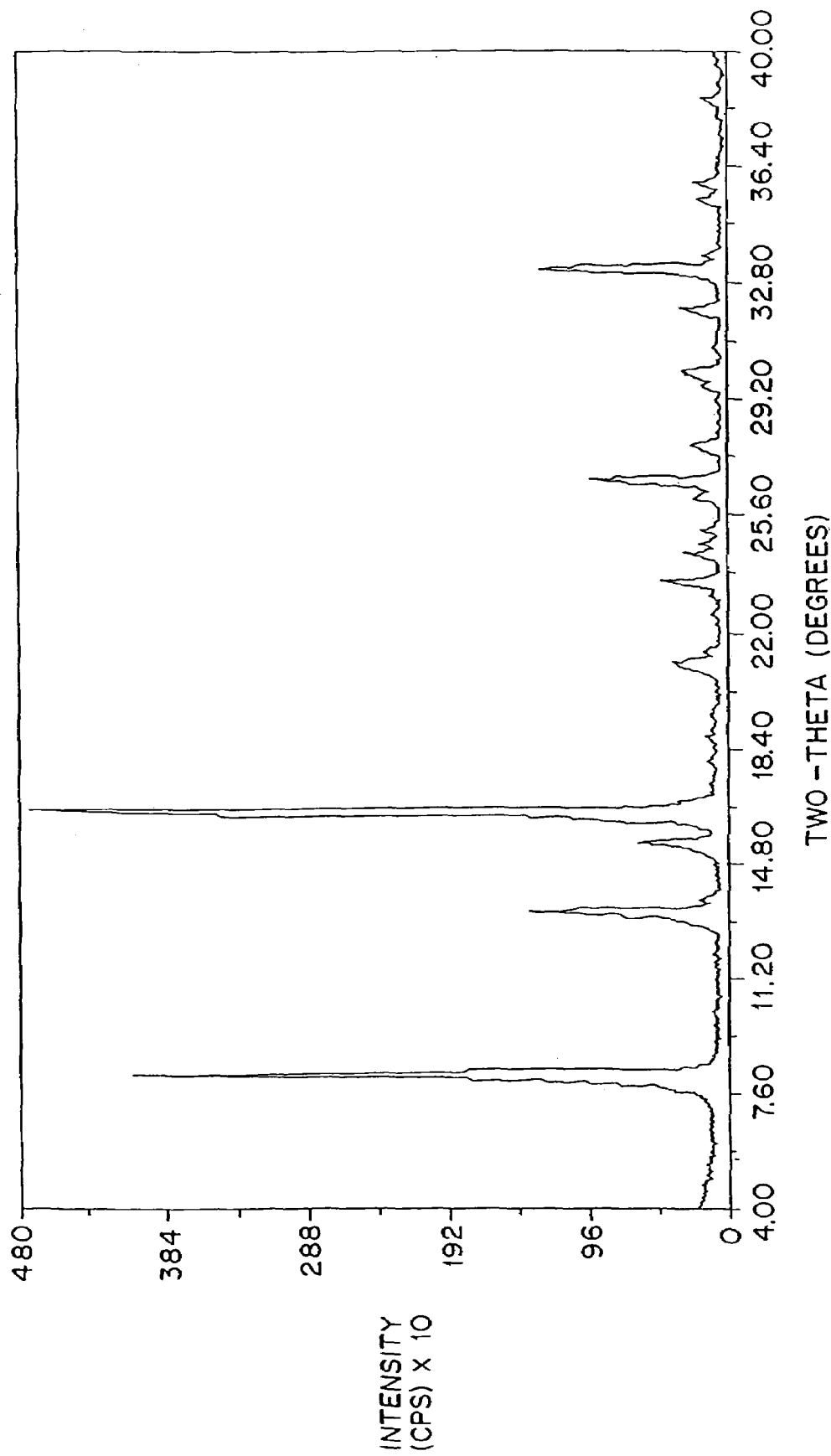

STABLE AMORPHOUS AMIFOSTINE COMPOSITIONS AND METHODS FOR THE PREPARATION AND USE OF SAME

1. FIELD OF INVENTION

The present invention relates to thermally-stable dosage forms of S-2-(3-aminopropylamino)ethyl dihydrogen phosphorothioate (amifostine), and to methods of making same. The reconstituted dosage forms of the invention are suitable for administration to humans, for example, as a radio- or chemoprotectant agent.

2. BACKGROUND OF THE INVENTION

The compound S-2-(3-aminopropylamino)ethyl dihydrogen phosphorothioate (which is also known as amifostine, ethiofos, Ethyol®, NSC 296961, and WR-2721 and which will hereinafter be referred to as "amifostine") and other aminothiol compounds are disclosed in U.S. Pat. No. 3,892, 824. These compounds were originally developed as antiradiation agents (radio-protectants), in particular to be used prior to exposure to x-ray or nuclear radiation, to protect against the harmful effects of such exposure which may be encountered during military conflicts.

In addition to its utility as a military antiradiation agent, amifostine has demonstrated excellent utility as a non-military radioprotectant and chemoprotectant, i.e., as a protectant administered prior to therapy to reduce the undesirable adverse effects which arise during the use of chemotherapy and radiation therapy in the treatment of cancer. Nygaard et al., eds, *Radioprotectors and Anticarcinogens*, Academic Press, Inc., New York, pp. 73-85 (1983); Grdina et al. *Carcinogenesis (London)* 6:929-931 (1985). In addition, these compounds have been reported to afford protection against the adverse effects of chemotherapeutic agents, for example, alkylating agents such as cisplatin, when administered before or concurrently with the chemotherapeutic agent. Jordan et al., *Exp. Mol. Pathol.* 36:297 (1982); Doz et al., *Cancer Chemother. Pharmacol.* 28:308 (1991). Similarly, it has been reported that amifostine has been used experimentally prior to therapy to protect HIV-infected patients (AIDS) from the harmful side effects of 3'-azido-3'-deoxythymidine (AZT) therapy. International Published Application WO 90/14007, published Nov. 29, 1990. Amifostine and its derivatives have been shown to exert these reported protective effects without affecting the beneficial properties of the administered therapeutic agents. This is, in the case of chemotherapy, believed to be due to the selective uptake of the protective thiol and other metabolites into normal tissue. Yuhas, *Cancer Res.* 40:1519-1524 (1980); Yuhas, *Cancer Treat. Rep.* 63:971-976 (1979).

Amifostine and related aminothiol compounds have also been shown to stimulate bone marrow growth. See, e.g., International Published Application WO 96/25045 published Aug. 22, 1996; and List et al., *Proc. Am. Soc. Clin. Oncol.* 15:449 [1403] [Abstract]. Currently, amifostine is in Phase II clinical trials as a bone marrow stimulant in patients suffering from myelodysplastic syndrome. Pre-exposure with aminothiol compounds is capable of causing the bone marrow function to more rapidly recover following chemotherapy. List et al. *Semin. Oncol.* 23 (4) Supp. 8:58-63 (1996).

Presently, amifostine is indicated to reduce the cumulative renal toxicity associated with repeated administration of cisplatin in patients with advanced ovarian or non-small cell lung cancer. *Physicians' Desk Reference* 52$^{nd}$ ed., p. 500-502 (1998).

Amifostine is considered a prodrug. Amifostine is metabolized to the cytoprotective free thiol by dephosphorylation catalyzed by alkaline phosphatase. See, e.g., Ryan, S. V., et al, *J. Clin. Pharm.* 36(4):365-373 (1996). Amifostine exerts protective effects without significantly affecting the beneficial properties of the administered therapeutic agents largely because of the selective uptake of the thiol into normal tissue.

In its most common use, amifostine is administered parenterally, including by bolus injection and intravenous infusion. Amifostine is also being developed for subcutaneous administration. Since these routes circumvent the protective barriers of the human body, exceptional purity of the dosage form must be achieved. Because the dosage form must be free of microoganisms and insoluble particulates, the process used in preparing it must embody Good Manufacturing Practices ("GMP") that will produce and maintain the required quality of the product in terms of sterility and therapeutic effectiveness. Sterility is especially important in the treatment of cancer and AIDS patients, because in many instances they are already immuno-compromised and therefor highly susceptible to infections.

The amifostine bulk drug (which is distinct from the dosage form) can exist as a bulk crystalline trihydrate which is believed to be relatively temperature stable. Such a crystalline form is described by Karle et al., *Acta Cryst.* C44:135-138 (1988). The bulk drug, however, is not sterile, and so cannot be reconstituted into a pharmaceutical product suitable for parenteral administration to humans.

Several methods of sterilizing bulk drugs are described in *Remington's Pharmaceutical Sciences*, 18$^{th}$ ed. (1990). These include, for example, steam sterilization, wherein a drug is exposed to high pressure steam at a minimum temperature of 121° C. This and other methods that require heating, however, cannot effectively be used to sterilize bulk crystalline amifostine. This is because crystalline amifostine loses water at about 70° C. to about 75° C. The loss of water facilitates degradation by a hydrolysis reaction that forms phosphoric acid and 2-[(3-aminopropyl)amino]ethane thiol. See e.g., Risley, J. M. and Van Etten, R. L., *Biochem. Pharmacol.* 35:1453-1458 (1986). Amifostine has thus been sterilized by dissolving it in an aqueous solution which is then sterilized by membrane filtration. Substantial practical problems related to the packaging of bulk, solid amifostine using the so-called "dry filling" or "powder filling" method were thus avoided. These problems include producing sterile amifostine bulk, the difficulty in the manual manipulation of powders, the need to mill the powders to acceptable particle size and flowability, difficulty in maintaining particle-free, aseptic conditions, and the difficulty in supplying the precise dosages into individual vials.

In solution, however, amifostine is again susceptible to degradation by hydrolysis. For this reason, a prior process has sterilized an amifostine solution by filtration, and then lyophilized (freeze-dried) the amifostine solution under the following conditions: about 5 mL of a solution of 100 mg/mL amifostine and 100 mg/mL mannitol placed in vial was loaded into a freeze-drier at 0° C. and then solidified at −45° C. The vials were kept at −45° C. for 2 hours, after which time the freeze drying chamber was evacuated to 100 μm Hg. The self temperature was then raised to 0° C. over 12 hours and then maintained at 0C for 2 hours. The shelf temperature was finally raised to 25° C., at which temperature the vials were kept for 24 hours. This method produced a sterile amorphous form of amifostine suitable for parenteral administration to a patient (which is hereinafter referred to as "Amorphous Amifostine I"). *Physicians' Desk Reference*, 51$^{st}$ ed. (1997) p.

485-486. This method also allowed easy production of vials containing predetermined amounts of sterile, lyophilized amifostine.

Unfortunately, Amorphous Amifostine I was thermally unstable and hydrolyzed over time at temperatures above 0° C. For example, a typical sample of Amorphous Amifostine I kept at 25° C. for about one month formed about 6 to 7 weight percent of the degradation product 2-[(3-aminopropyl) amino]ethane thiol. This was the state of the art when the amorphous form of amifostine was approved by regulatory authorities as having a shelf life of 24 months when stored at temperatures of between about 2° C. and 8° C. See e.g., Ethyol® European Summary of Product Characteristics (1997) ("Ethyol® SmPC"). In fact, the Amorphous Amifostine I dosage form was generally packaged, shipped, and stored at temperatures below about 8° C. Further, in the United States, the amorphous form of amifostine was approved by the Food and Drug Administration as having a shelf life of 15 months when stored at temperatures of between about 2° C. and 8° C.

Temperature instability imposes upon manufacturers and users packaging, storage and shipping requirements that increase the cost of handling the drug and make its use by hospitals and clinics more difficult, and may even prevent its use in developing countries which often lack temperature controlled storage maintenance capabilities.

In recognition of the need for a dosage form of amifostine that is more thermally-stable than Amorphous Amifostine I, research has been directed at finding new stable and sterile dosage forms of amifostine. For example, Jahansouz and coworkers, studied the stability of amifostine and suggested that temperature instability of Amorphous Amifostine I is related to its degree of water content. Jahansouz, H., et al. Pharm. Res. 7(9):S195 (1990) [Abstract].

Recently, instead of attempting to increase the stability of dosage forms of amorphous amifostine such as Amorphous Amifostine I, researchers focused on creating stable and sterile crystalline dosage forms. For example, it was reported that amifostine "undergoes solid state transitions from the amorphous to crystalline phases by treatment of the freeze-dried products with varying humidity." Further, the stability of rehydrated forms of amifostine was allegedly increased by the addition of certain excipients. Zadeii, J. M., et al., Pharm. Res. 8(10):S172 (1991) [Abstract]. This abstract does not, however, describe the rehydration process in any detail, nor does it describe the degree of stabilization provided by the two excipients it discloses. In addition, the abstract provides no detail as to how and when particular excipients should be combined with amifostine to yield the alleged more stable rehydrated forms (i.e., whether the excipients were combined with amifostine prior to, during, or after its rehydration), or whether the process should differ for different excipients. Finally, a novel dosage form of sterile, thermally-stable crystalline amifostine was discovered. U.S. Pat. Nos. 5,424,471 and 5,591,731.

Presently, that sterile crystalline dosage form of amifostine is sold under the trade name Ethyol®. Physicians' Desk Reference, 52$^{nd}$ ed. (1998) p. 500-502. A crystal structure and preparation of a dosage form, which exhibits greater thermal stability than Amorphous Amifostine I, is described by U.S. Pat. Nos. 5,424,471 and 5,591,731. Generally, this thermally-stable crystalline dosage form is made by dissolving bulk amifostine in a solvent solution (that allows precipitation of amifostine upon cooling below 0° C.), followed by sterilization, precipitation and lyophilization of the compound. Because the crystallinity, and hence the stability, of this amifostine dosage form requires three water molecules per molecule, the lyophilization used to provide the final product must be carefully controlled to ensure the required degree of hydration. Once made, the stable crystalline dosage form may be stored at room temperature with minimal degradation: it exhibits less than 2 weight percent degradation when kept at 40° C. for 14 days. U.S. Pat. No.5,591,731.

Although newly developed sterile crystalline dosage forms of amifostine reduce or eliminate many of the problems associated with Amorphous Amifostine I, production of such can be costly, difficult and/or dangerous. For example, the production of crystalline Ethyol® requires the use of explosive solvents which must be handled with care and strictly isolated from oxygen. Such solvents also contain impurities not typically found in water that must be removed to ensure that the dosage form is suitable for reconstitution and administration to a patient. For example, ethanol often contains acetone, methanol, $H_2SO_4$, $MnO_4$, and other toxic residues. See e.g., Aldrich Catalog (1998-1999), pages 746-747. The production of crystalline amifostine dosage forms further requires long lyophilization drying times in order to ensure precise amifostine hydration.

In view of the above-described and other difficulties associated with the production of sterile crystalline dosage forms of amifostine, there remains a need for a stable, sterile amorphous dosage form, as well as an efficient and inexpensive means of its production.

The invention also encompasses non-sterile and/or bulk thermally-stable amorphous amifostine. To applicants' knowledge, to date an amorphous thermally-stable amifostine has not been previously disclosed. In preferred embodiments, the invention encompasses thermally-stable dosage forms of amifostine.

3. SUMMARY OF THE INVENTION

The present invention encompasses non-sterile and/or bulk thermally-stable amorphous amifostine. To applicants' knowledge, amorphous thermally-stable amifostine has not been previously disclosed. In preferred embodiments, the invention encompasses thermally-stable dosage forms of amifostine.

The invention encompasses the following thermally-stable and sterile dosage forms: a dosage form which comprises amorphous amifostine; an amorphous dosage form which comprises amifostine; and a dosage form that is suitable for reconstitution with a pharmaceutically acceptable vehicle into an injectable particulate-free drug product suitable for parenteral administration to a subject, which comprises amorphous amifostine.

The invention also encompasses a room temperature stable dosage form comprising sterile amorphous amifostine.

The invention also includes a room temperature stable amorphous dosage form comprising sterile, amorphous amifostine.

This invention is further directed to a refrigerated stable dosage form comprising sterile amorphous amifostine.

The dosage forms of this invention may comprise a stabilizer. It is preferred that the molar ratio of stabilizer to amifostine be between about 0.05 and about 5.0, more preferably between about 0.1 and about 1.0, and most preferably between about 0.2 and about 0.5. Preferred stabilizers are compounds having amide or amino acid moieties. A specific preferred stabilizer is nicotinamide.

The dosage form of the present invention may also comprise an excipient. Suitable excipients include, but are not limited to, sodium chloride, citric acid, tartaric acid, gelatin, polyvinylpyrrolidone (PVP), dietylenetriamine-pentaacetic acid (DTPA), ethylenediamine-tetraacetic acid (EDTA), sodium deoxycholate, sodium taurocholate, and carbohydrates such as, but not limited to, dextrose, sucrose, sorbitol, inositol, dextran, mannitol, and carboxymethyl cellulose sodium salt. Finally, the dosage forms may also contain up to about 20 percent water without significant loss of thermal stability.

A preferred dosage form of the invention comprises amorphous amifostine, nicotinamide, and PVP.

The present invention is further directed to a process of making a thermally-stable and sterile amorphous dosage form of amifostine, and to the products of that process.

3.1 DEFINITIONS

As used herein, the terms "bulk amifostine" or "bulk drug" mean a form of amifostine which is used in preparing dosage forms, but is not suitable for parenteral administration to a patient. The term encompasses amifostine as disclosed by U.S. Pat. No. 3,892,824, including, but not limited to, mono-, di- and trihydrate forms of amifostine.

As used herein, the term "crystalline," when used to describe a component or product, means that the component or product is crystalline as determined by x-ray diffraction. See, e.g., *Remington's Pharmaceutical Sciences*, 18$^{th}$ ed. page 173; *The United States Pharmacopeia*, 23$^{rd}$ ed. (1995) pages 1843-1844.

As used herein, the term "amorphous" means that the component or product in question is not crystalline as determined by x-ray diffraction.

It should be recognized that a multi-component product, e.g., a product having amifostine and excipients and/or stabilizers, may have crystalline and amorphous components, e.g., amorphous amifostine and crystalline excipients and/or stabilizers.

As used herein, the terms "degradation" and "decomposition" when used in connection with amifostine refer to the production of 2-[(3-aminopropyl)amino]ethane thiol (WR1065) and phosphoric acid from amifostine.

As used herein, the term "Amorphous Amifostine I" means a dosage form of amifostine that contained amorphous amifostine and which gave an average of about 3.5% degradation product (i.e., 2-[(3-aminopropyl)amino]ethane thiol) at about 5° C. for 2 years. An example of the preparation of Amorphous Amifostine I is described in the Background of the Invention section above.

As used herein, the term "Amorphous Amifostine II" refers to a dosage form of this invention which is suitable for reconstitution and parenteral administration to a patient. In particular, Amorphous Amifostine II refers to a dosage form of amorphous amifostine as described herein.

As used herein, the terms "stability" and "thermal stability" refer to the ability of a composition to withstand degradation or decomposition when kept at a particular temperature for a specified period of time, preferably under inert atmosphere. Appropriate means of determining stability are defined herein.

As used herein, the term "thermally-stable" means more stable than Amorphous Amifostine I (i.e., the previously commercial amorphous dosage form described in the Background of the Invention section above).

As used herein, the term "stabilizer" means a compound or mixture of compounds that when mixed in a sufficient amount with bulk amifostine, and used in the production of an amifostine dosage form, increases the thermal-stability of the dosage form, for example by reducing the amount of 2-[(3-aminopropyl)amino]ethane thiol formed by it over time.

As used herein, a range of numbers or values defined by the use of the term "between" includes the particular numbers or values used to describe that range.

As used herein, the term "month" means a period of time of between about 26 days and about 33 days.

As used herein, the term "weight percent" when used to describe the amount of degradation product in a dosage form means the weight of degradation product based upon the weight of amifostine originally in that dosage form.

As known to those skilled in the art, accelerated studies can be used for the determination of stabilities and these temperatures. See, e.g., L. Lachman, et al. *The Theory and Practice of Industrial Pharmacy* pages 766-67 (1986). The less a compound or mixture of compounds degrades when kept at a particular temperature for a particular time, the more thermally-stable it is.

As used herein, the terms "refrigeration" or "refrigeration conditions" mean the maintenance of a temperature of between about 1° C. and about 8° C.

As used herein, the terms "freeze" or "freezer conditions" mean the maintenance of a temperature of below about 0° C., particularly between about 0° C. and about −20° C.

As used herein, the term "particulate-free" means a solution that is sterile, suitable for bolus injection, intravenous infusion, or subcutaneous administration, and meets the particulate matter test described in *U.S. Pharmacopia*, page 1816 (23$^{rd}$ ed., 1995). Specifically, a solution is particulate-free if the average number of particles having a diameter of greater than 10 µm in the solution does not exceed 6000 per container and the average number of particles having a diameter of greater than 25 µm in the solution does not exceed 600 per container.

3.2 FIGURES

FIG. 1. Powder x-ray diffraction pattern of crystalline amifostine prepared as described by U.S. Pat. No. 5,591,731.

Figure 2:
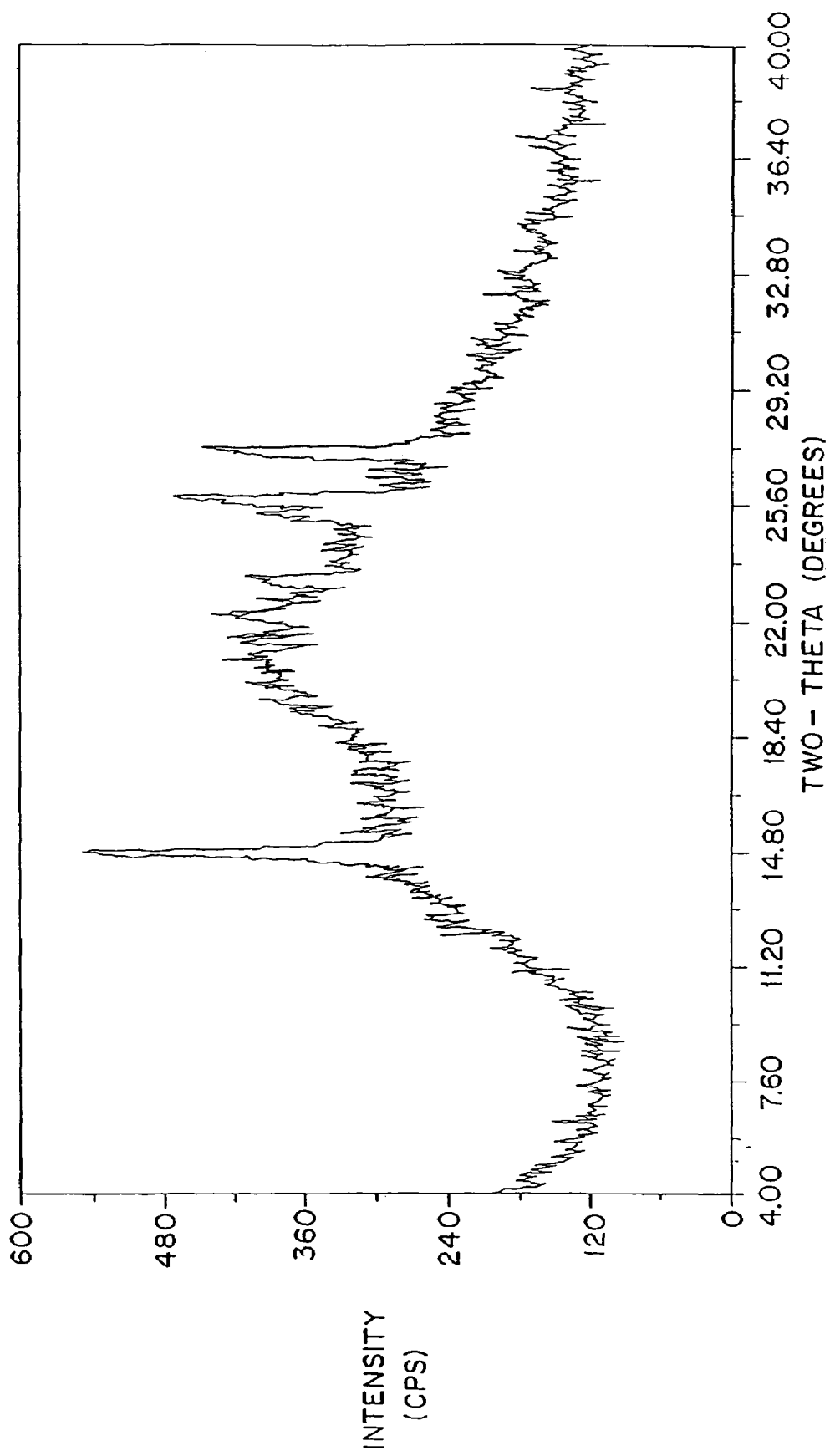

FIG. 2. Powder x-ray diffraction pattern of an amorphous amifostine dosage form of the present invention wherein nicotinamide is used as a stabilizer (8:1 amifostine to nicotinamide weight ratio). This diffraction pattern contains clearly discernable peaks where 2θ is approximately equal to the following: 7.9, 13.0, 16.1, 27.4 and 32.8.

Figure 3:
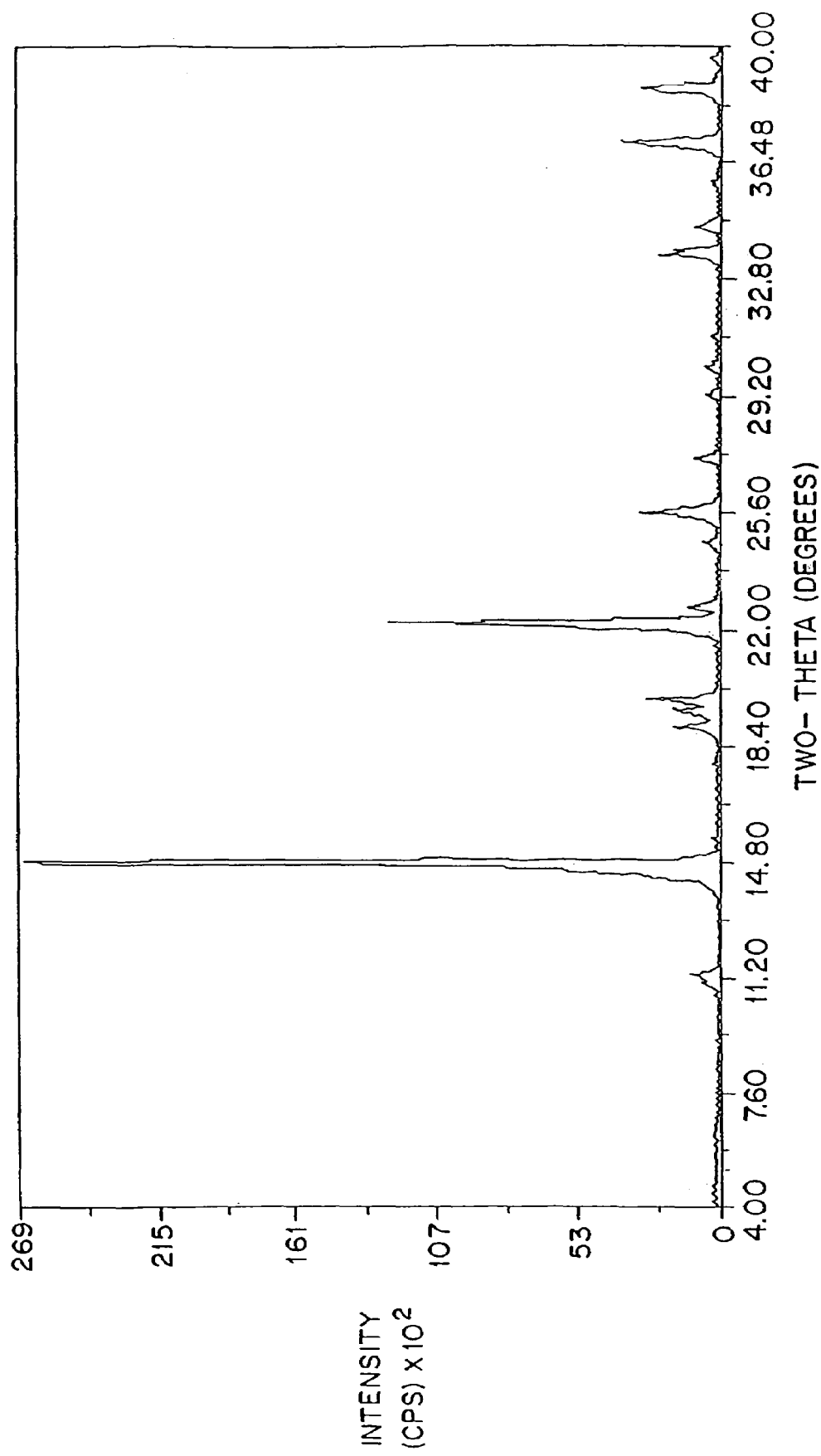

FIG. 3. Powder x-ray diffraction pattern of nicotinamide.

Figure 4:
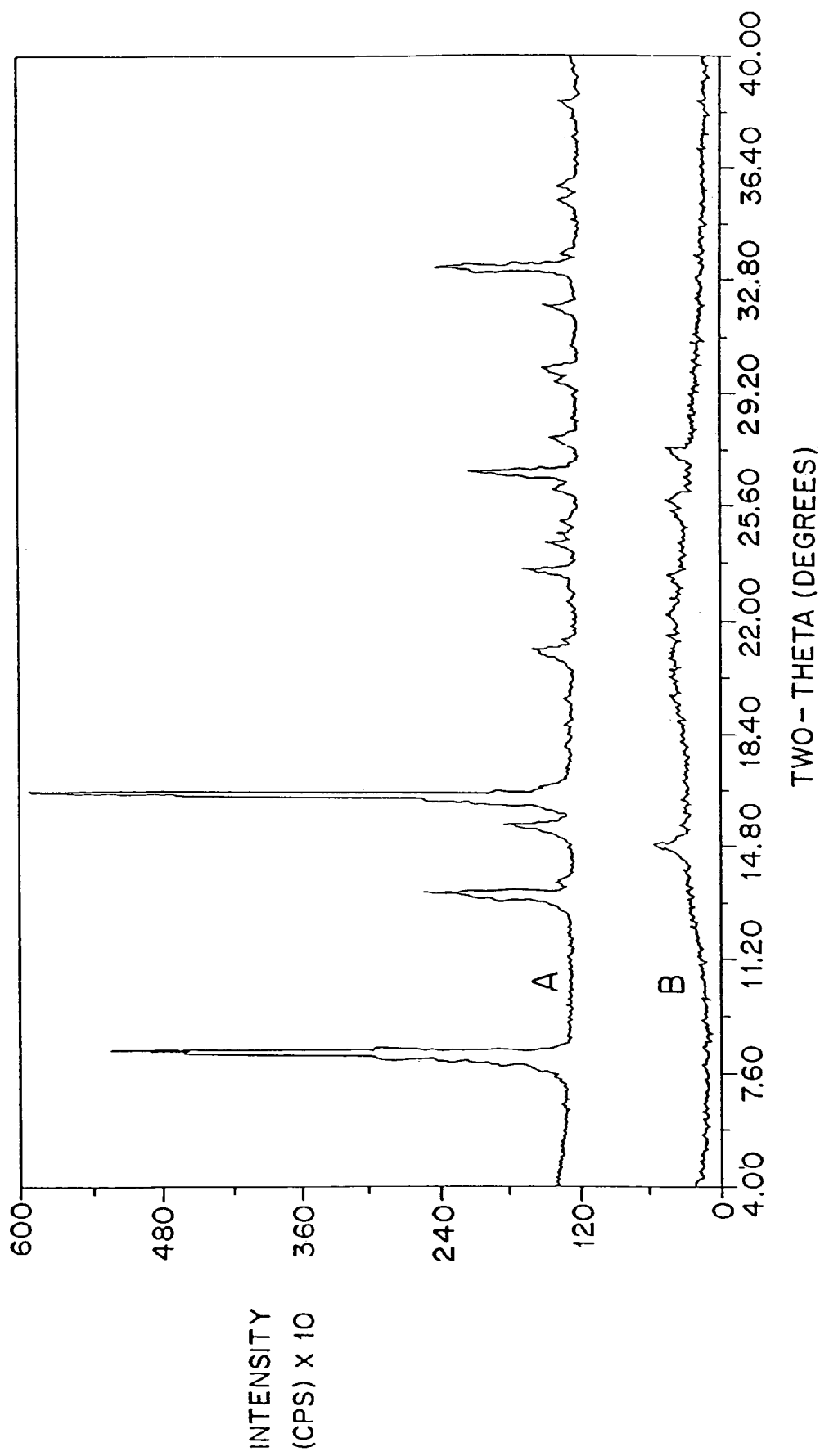

FIG. 4. Comparison of the powder x-ray diffraction patterns of (A) crystalline amifostine prepared as described by U.S. Pat. No. 5,591,731; and (B) that of an amorphous amifostine dosage form of the present invention wherein nicotinamide is used as a stabilizer (8:1 amifostine to nicotinamide weight ratio).

4. DETAILED DESCRIPTION OF THE INVENTION

Prior to the present invention, the available pharmaceutically useful dosage form of amorphous amifostine (Amorphous Amifostine I) was thermally unstable, and would, for example, typically yield about 6 weight percent degradation product (i.e., 2-[(3-aminopropyl)amino]ethane thiol) when kept at 25° C. for one month. Because of its temperature instability, Amorphous Amifostine I was typically shipped and stored at low temperatures (generally 8° C., e.g., about 5±3° C.) in order to prevent its degradation. Now, the present invention provides a dosage form of amorphous amifostine (Amorphous Amifostine II) that is unexpectedly more thermally-stable than Amorphous Amifostine I.

The present invention can be applied to other aminoalkyl dihydrogen phosphorothiates, and thus provides a more stable dosage forms of these aminoalkyl dihydrogen phosphorothioates. Aminoalkyl dihydrogen phosphorothioates suitable for use in the present invention include, but are not limited to, S-2-(3-aminopropylamino)ethyl dihydrogen phosphorothioate (amifostine), S-2-(3-methylaminopropylamino)ethyl dihydrogen phosphorothioate (WR-3689), S-2-(3-ethylaminopropylamino)ethyl dihydrogen phosphorothioate, S-2-(3-aminopropylamino)-2-methylpropyl dihydrogen phosphorothioate, S-2-(2-aminoethylamino)-2-ethyl dihydrogen phosphorothioate, S-2-(4-aminobutylamino)-2-ethyl dihydrogen phosphorothioate, S-2-(5-aminopentylamino)-2-ethyl dihydrogen phosphorothioate, S-2-(6-aminohexylamino)-2-ethyl dihydrogen phosphorothioate, S-2-(2-methylaminoethylamino)-2-ethyl dihydrogen phosphorothioate, S-2-(3-methylaminopropylamino)-2-ethyl dihydrogen phosphorothioate, 1-propanethiol-3-[[3-(methylamino)propyl]amino]-dihydrogen phosphothiorate) (WR-151327) and its free thiol form (WR-151326), and the disulfide [2-[(aminopropyl)amino]ethanthiol]-N,N'-dithioidi-2,1-ethanediyl)bis-1,3-propanediamine) (WR-33278). In a preferred embodiment of the invention, the aminoalkyl dihydrogen phosphorothioate is amifostine.

In particular, the present invention provides a pharmaceutical dosage form of amorphous amifostine suitable for reconstitution and parenteral administration to a patient that can be conveniently shipped, stored and handled at room temperature and refrigerated temperatures with less product degradation than Amorphous Amifostine I. The dosage forms of this invention (e.g., Amorphous Amifostine II) thus provide a solution to a long felt need: the invention allows relatively low cost amifostine dosage forms to be more easily shipped to, and more easily stored in, hospitals and clinics which lack temperature controlled storage and maintenance capabilities required for Amorphous Amifostine I.

The present invention is based in part upon the unexpected discovery that particular amounts of certain compounds when mixed with amifostine can be used to produce amorphous dosage forms with reduced rates of decomposition. These certain compounds are herein referred to as "stabilizers." Without being limited by theory, it is believed that these stabilizers form van der Waals or a similar weak intermolecular interactions with the amifostine sulfur atom. These interactions may prevent the activation (e.g., protonation) of the sulfur atom. These stabilizers may also inhibit the interaction of water with, and prevent nucleophilic attack upon, the amifostine phosphorous atom.

Because the presence of some stabilizers have been found to interfere with the measurement of the amifostine content of dosage form samples, the stability of a dosage form comprising a stabilizer is preferably determined by measuring the formation of amifostine degradation or decomposition products as a function of temperature and time. Such products include, but are not limited to, 2-[(3-aminopropyl)amino] ethane thiol (the primary degradation product of amifostine) and phosphoric acid.

It has also been discovered that the stability of the dosage forms of amorphous amifostine is dependent upon the freeze drying process used for its preparation, and that the simple mixing of amifostine and a stabilizer does not necessarily yield a more stable dosage form. Even more unexpected is the discovery that, contrary to the teaching of the prior art, dosage forms of amorphous amifostine comprising different amounts of water may be thermally-stable.

Consequently, this invention is directed to thermally-stable dosage form of amifostine. In particular, it is directed to a dosage form that exhibits less than 5 weight percent degradation when maintained at 40° C. for one week, said weight percent based upon total weight of amifostine; preferably less than 4 weight percent degradation when maintained at 40° C. for one week, said weight percent based upon total weight of amifostine; and more preferably less than 3 weight percent degradation when maintained at 40° C. for one week, said weight percent based upon total weight of amifostine.

In another embodiment, the dosage form of this invention exhibits less than 5 weight percent degradation when maintained at 25° C. for one month, said weight percent based upon total weight of amifostine; preferably less than 4 weight percent degradation when maintained at 25° C. for one month, said weight percent based upon total weight of amifostine; more preferably less than 3 weight percent degradation when maintained at 25° C. for one month, said weight percent based upon total weight of amifostine; and most preferably less than 2 weight percent degradation when maintained at 25° C. for one month, said weight percent based upon total weight of amifostine.

In a further embodiment, the dosage form of this invention exhibits less than 3 weight percent degradation when maintained at 5° C. for about two years, said weight percent based upon total weight of amifostine; preferably less than 2 weight percent degradation when maintained at 5° C. for about two years, said weight percent based upon total weight of amifostine; and more preferably less than I weight percent degradation when maintained at 5° C. for about two years, said weight percent based upon total weight of amifostine.

In a further embodiment, this invention is directed to a thermally-stable dosage form comprising substantially amorphous amifostine. Preferably, the thermally-stable dosage form comprises amifostine that is at least 80% amorphous by weight. More preferably, the thermally-stable dosage form comprises amifostine that is at least 90% amorphous by weight. This invention is also directed to a thermally-stable dosage form comprising amorphous amifostine.

In another embodiment, this invention is directed to a thermally-stable, substantially amorphous dosage form comprising amifostine. Preferably, the thermally-stable dosage form is at least 80% amorphous by weight. More preferably, the thermally-stable dosage form is at least 90% amorphous by weight. This invention is also directed to an amorphous thermally-stable dosage form comprising amifostine.

Another embodiment of this invention provides a thermally-stable dosage form that contains an amount of water between about 0 and about 20 weight percent, preferably between about 0 and about 15 weight percent, and more preferably between about 0.5 and about 6 weight percent.

The present invention is further directed to thermally-stable dosage form of amifostine which comprises one or more stabilizers and optionally one or more excipients. Preferably, the molar ratio of stabilizer to amifostine is between about 0.05 and about 5.0, more preferably between about 0.1 and about 1.0, and most preferably between about 0.2 and about 0.5 weight percent.

As above, the thermally-stable dosage form which comprises one or more stabilizers and optionally one or more excipients may also contain an amount of water between about 0 and about 20 weight percent, preferably between about 0 and about 15 weight percent, and more preferably between about 0.5 and about 6 weight percent. Each of the dosage forms of the invention can be produced as an elegant cake product (e.g., dissolves in less than 60 seconds).

This invention is further directed to a process of making a thermally-stable dosage form of amorphous amifostine. In this process, amifostine may be combined with one or more stabilizers and/or one or more excipients. As made clear below, this method encompasses all means by which amifostine, water, stabilizers, and excipients may be combined. For example, amifostine and a stabilizer may be combined in any order prior to, during, formed in situ, or after lyophilization of bulk amifostine. Because several different stabilizers may be used to prepare the dosage form of this invention, each may be combined with amifostine together or separately in any order during its preparation.

It has been found, however, that an especially economical and efficient means of creating a thermally-stable dosage form of amorphous amifostine (e.g., Amorphous Amifostine II) involves the formation of a single solution comprising bulk amifostine, a stabilizer, and optionally an excipient. According to the present invention, vials are loaded with a sterile filtered solution comprising amifostine and optionally a stabilizer and/or excipient. A particular advantage of this processes is that the solvent used to form the solution may be pure water, instead of the ethanol/water mixture required for the production of sterile crystalline amifostine compositions. This invention, however, encompasses the use of other solvents, and in particular aqueous solvents having pHs of between about 3 and about 11, more preferably between about 6 and about 9, and most preferably between about 7 and about 8. Bulk amifostine is known to be more stable in basic solutions. Risley, J. M. and Van Etten, R. L., *Biochem. Pharmacol.* 35:1453-1458 (1986).

After being filled with the amifostine solution, the vials are loaded into a freeze-dryer which is then evacuated. The freeze-drier may be pre-chilled. The vials are kept at a temperature and pressure sufficient to remove a significant portion of the solvent. Typically, and as is well known to those skilled in the art, the temperature of the vials is increased near the end of the freeze-drying cycle to ensure that the desired amount of solvent is removed. The novel drying process described in detail below, however, has been found to form cake products that have consistencies and stabilities previously thought not to be possible for non-crystalline dosage forms. Furthermore, the drying process of this invention helps ensure that if the dosage form of this invention (e.g., Amorphous Amifostine II) is to contain a stabilizer, the maximum stabilizing effect of that stabilizer is obtained.

Although the following freeze drying conditions are not meant to be limiting, it has been found that Amorphous Amifostine II is most easily formed when the freeze drying, or lyophilization, process comprises the following steps: freezing the amifostine solution during a freezing cycle to form a frozen mixture; evacuating (vacuum) the lyophilization chamber; and drying the frozen mixture during a primary drying cycle which comprises at least one primary drying stage. The process may further comprise further drying using a secondary drying cycle comprising at least one secondary drying stage, and/or a desiccating means such as the use of desiccants, a desiccator, desiccating stoppers, and the like. Upon completion of the lyophilization, an inert gas such as nitrogen is preferably added to the vials containing the lyophilized dosage form.

It is preferred that the freezing cycle last from between about 1 hour and about 15 hours, more preferably from between about 2 hours and about 10 hours, and most preferably between about 5 hours and about 8 hours. It is preferred that temperature of the freeze dryer during the freezing cycle be maintained at an average of between about $-70°$ C. and about $-10°$ C., more preferably between about $-65°$ C. and about $-30°$ C., and most preferably between about $-55°$ C. and about $-40°$ C.

Near the end, or upon completion, of the freezing cycle, the freeze drier is evacuated such that the frozen mixtures are exposed to a pressure (vacuum) sufficient to remove the solvent (which may exist in a liquid and/or solid phase) at the average temperature of the primary drying cycle. When the solvent is water, preferred pressures are less than the vapor pressure of water at the particular drying cycle temperature. Such vapor pressures are provided by the *CRC Handbook of Chemistry and Physics*, page D-198 ($64^{th}$ ed; 1983-1984).

The freeze drier may instead be evacuated upon or following commencement of the primary drying cycle. It is during this cycle that most of the water or solvent in the frozen mixture is removed. This cycle is characterized by an average pressure, average temperature and duration, but may contain one or more stages, each of which is characterized by an average pressure, average temperature and duration. Typically, however, it is preferred that the primary drying cycle comprise only one stage that lasts from between about 8 hours and about 100 hours, more preferably from between about 16 hours and about 86 hours, and most preferably between about 24 hours and about 72 hours. It is preferred that temperature of the freeze dryer during the primary drying cycle be maintained at an average of between about $-45°$ C. and about $10°$ C., more preferably between about $-35°$ C. and about $0°$ C., and most preferably between about $-30°$ C. and about $-10°$ C.

The primary drying cycle is optionally followed by a secondary drying cycle, during which residual water or solvent is removed. This cycle is characterized by an average pressure, average temperature and duration, but may contain one or more stages, each of which is characterized by an average pressure, average temperature and duration. Typically, however, it is preferred that the secondary drying cycle comprise only one stage that lasts from between about 0.5 hours and about 48 hours, more preferably from between about 2 hours and about 36 hours, and most preferably between about 6 hours and about 24 hours. It is preferred that temperature of the freeze dryer during the secondary drying cycle be maintained at an average of between about $-25°$ C. and about $40°$ C., more preferably between about $-15°$ C. and about $40°$ C., and most preferably between about $0°$ C. and about $35°$ C.

Instead of a secondary drying cycle, or in addition thereto, an optional desiccating means may be used to further dry the dosage forms. Desiccating means include, but are not limited to, the use of desiccants, desiccators, desiccating stoppers, and the like.

For example, an elegant cake product has been found to form if vials are initially loaded into a freeze drier kept at a temperature of between about $-20°$ C. and about $15°$ C., after which the freeze drier shelf temperature is decreased to between about $-70°$ C. and about $-30°$ C. over a period of time that allows uniform freezing of the amifostine/stabilizer solution. The freeze drying chamber is then evacuated to cause removal of the solvent. It is preferred that the pressure be maintained at between about 10 μm Hg to about 500 μm Hg, more preferably between about 75 μm Hg and about 200 μm Hg if the solvent is water. Typically, after the pressure is allowed to equilibrate the temperature of the chamber is increased to a temperature of between about $-35°$ C. to about $25°$ C. for a time sufficient to remove most of the solvent. As described in more detail below, it has been found that a suitable cake product is best formed by exposing the vials to a variety of different temperatures and pressures over periods of time ranging from minutes to days.

Completion of the lyophilization process yields a stable amifostine dosage form comprising amorphous amifostine that is suitable for reconstitution into a particulate-free solution suitable for parenteral administered to a patient. It is preferred, however, that the freeze-drying chamber be filled with an inert gas such as nitrogen, argon or xenon prior to the sealing of the vials. It has been found that this facilitates the stability of the dosage form. The vials can then be stored and shipped at a temperature that depends upon the desired shelf life of the dosage form. A particularly suitable temperature is between about 0° C. to about 25° C., most preferably about 4° C.

It has been found that by varying the temperature, time and number of drying cycles, products with different stabilities and water contents can be obtained, all of which are encompassed by the present invention. Karl Fisher titration, for example, may be used to determine water content.

According to the present invention, any amount of stabilizer may be combined with amifostine just so long as that amount is sufficient to increase the thermal stability of the lyophilized product. It is preferred, however, that between about 0.05 mol to about 5.0 mol of stabilizer be used per 1.0 mol pure bulk crystalline amifostine trihydrate (FW=268 g/mol). This amount is more preferably between about 0.1 mol to about 1.0 mol, and most preferably between about 0.2 mol to about 0.5 mol bulk crystalline amifostine trihydrate. As those skilled in the art will recognize, however, the exact amount of stabilizer added depends upon a variety of factors, including the chemical and pharmaceutical characteristics of the stabilizer and the purity and water content of the bulk amifostine. The latter is particularly noteworthy, as bulk amifostine is available in crystalline forms, and in varying degrees of hydration. Bulk amifostine has been described as a crystalline form having from one to three water molecules per molecule, but may also exist in other forms. Bulk amifostine may be made by the process disclosed in U.S. Pat. No. 3,892,824, which is hereby incorporated by reference.

Stabilizers of the present invention are compounds or mixtures of compounds that are pharmaceutically acceptable and when combined with amifostine do not facilitate its degradation in solution yet enhance its stability when stored as a solid at room temperature. Suitable compounds include amides and amines such as, but are not limited to, nicotinamide, derivatives of nicotinamide, nicotinic acid, derivatives of nicotinic acid, and a variety of natural and synthetic amino acids and amino acid derivatives including, but not limited to, glycine, alanine, valine, leucine, isoleucine, phenylalanine, tryptophan, and asparagine.

Preferred stabilizers are nicotinamide, derivatives of nicotinamide, nicotinic acid, and derivatives of nicotinic acid. When nicotinamide is used as a stabilizer, it is preferably used in an amifostine to nicotinamide weight ratio of between about 2:1 and about 12:1, more preferably between about 4:1 and about 10:1. A most preferred weight ratio is about 8:1 (amifostine to nicotinamide).

It has been found that in order to, obtain an elegant cake upon lyophilization of a amifostine/stabilizer solution, the concentration of bulk amifostine should be between about 10 mg/mL to about 200 mg/ml, more preferably between about 50 mg/mL to about 150 mg/ml, and most preferably between about 75 mg/mL to about 125 mg/ml. The preferred concentration of stabilizer(s) may be determined from the preferred amifostine-to-stabilizer molar ratios provided above. As those skilled in the art will quickly recognize, the solubility of the desired stabilizer(s), readily determined from the literature, may also play a role in determining desired concentrations.

It is important to note that when used in combination with certain lyophilization methods, some stabilizers and concentrations of stabilizers can yield crystalline or partially crystalline, rather than purely amorphous, products. For example, when nicotinamide is used as a stabilizer in a weight ratio of 4:1 (amifostine to nicotinamide) under lyophilization conditions encompassed by this invention, a crystalline dosage form can sometimes result. Further, a dosage form with crystalline or partially crystalline stabilizer(s) and/or excipient(s) can also result. The present invention is concerned, however, with amorphous dosage forms or dosage forms containing amorphous amifostine.

As mentioned above, lyophilization of the bulk amifostine may optionally occur in the absence of a stabilizer. If it is done in the absence of a stabilizer, the stabilizer may be added following lyophilization. Similarly, excipients may be added to the dosage forms of the present invention either before, during, or after sterilization and lyophilization of the bulk amifostine. Excipients found useful for this purpose, often in combination, include, but are not limited to, sodium chloride, citric acid, tartaric acid, gelatin, polyvinylpyrrolidone (PVP), dietylenetriamine-pentaacetic acid (DTPA), ethylenediamine-tetraacetic acid (EDTA), sodium deoxycholate, sodium taurocholate, and carbohydrates such as, but not limited to, dextrose, sucrose, sorbitol, inositol, dextran, mannitol, and carboxymethyl cellulose sodium salt, although mannitol is not preferred.

A specific preferred excipient is PVP, which is commercially available in a variety of different viscosity-average molecular weights. Polyvinylpyrrolidone having a viscosity-average molecular weight of 30 (PVP30) is a specific preferred excipient. When PVP is used as an excipient, it is preferably used in an amifostine to PVP weight ratio of between about 2:1 and about 50:1, more preferably between about 5:1 and about 15:1. A most preferred weight ratio is about 10:1 (amifostine to PVP).

In addition to the excipients mentioned herein, others known to those skilled in the art can be used. It is preferred that the excipient not be a source of free phosphate, however, as this has been reported to facilitate the degradation of amifostine. See, e.g., Zadeii, J. M., et al., *Pharm. Res.* 8(10):S172 (1991).

Whatever excipient is incorporated into the present formulations, that excipient must be sterile when added, or sterilized during the same process that sterilizes the amifostine. An embodiment of the present invention includes a sterilization step. Sterilization may be affected, for example, by sterile filtering a solution, e.g., through a 0.2 µm pore size filter. Other methods of sterilizing known to those skilled in the art may also be employed. Suitable sterile and non-sterile excipients are commercially available from: EM Industries, Inc., Hawthorne, N.Y.; J.T Baker, Inc., Hayward, Calif.; Spectrum Quality Products, Inc., Gardena Calif.; Fisher Scientific International, Inc., Hampton N.H.; Aldrich Chemical Co., Inc., Milwaukee Wis.; Abbott Laboratories, Inc., North Chicago Ill.; Baxter Healthcare Corporation, Deerfield Ill.; and Amresco, Inc., Cleveland Ohio.

The dosage form of the invention may be provided in single dose container forms by. aseptically filling suitable containers with the sterile solution to a prescribed amifostine content as described above, or in multiple dose containers. It is intended that these filled containers will allow rapid dissolution of the solid composition upon reconstitution with appropriate sterile diluents in situ, giving an appropriate sterile solution of desired amifostine concentration for administration. As used herein, the term "suitable containers" means a container capable of maintaining a sterile environment, such as a vial, capable of delivering a vacuum dried product hermetically sealed by a stopper means. Additionally, suitable containers implies appropriateness of size, considering the volume of solution to be held upon reconstitution of the vacuum dried composition; and appropriateness of container material, generally Type I glass. The stopper means employed, e.g., sterile rubber closures or an equivalent, should be understood to be that which provides the aforementioned seal, but which also allows entry for the purpose of introduction of diluent, e.g., sterile Water for Injection, USP, Normal Saline, USP, or 5% Dextrose in Water, USP, for the reconstitution of the desired amifostine solution. These and other aspects of the suitability of containers for pharmaceutical products such as those of the invention are well known to those skilled in the practice of pharmaceutical arts.

The sterile, thermally-stable pharmaceutical compositions, (dosage forms) of the present invention are suitable for parenteral administration, for example, intravenous, intramuscular, intracavitary, intrathecal, and subcutaneous injections. These dosage forms have enhanced temperature stability over the prior dosage forms of amorphous amifostine, have good physical appearance, and are efficacious in the prevention and treatment of radiation damage and chemotherapy damage.

5. EXAMPLES

The following examples are intended to be illustrative of the present invention and should not be construed, in any way, to be a limitation thereof.

5.1. Example 1

Stable Amorphous Amifostine Dosage Form Comprising Nicotinamide

An aqueous solution of 100 mg/mL amifostine and 12.5 mg/mL nicotinamide (Aldrich) is sterile filtered at 25° C. through a 0.2 μm filter, and then divided into 5 mL aliquots, .each of which is transferred to 10 mL vials. Lyophilization stoppers are placed on the vials and the samples are loaded onto the freeze-dryer shelf maintained at 5° C. The shelf temperature is decreased to −45° C. over 60 minutes, at which temperature it is kept for about 3 hours. The freeze-dryer condenser is then turned on and chamber is evacuated to about 100 μm Hg. After the chamber vacuum has equilibrated, the shelf temperature is ramped to −25° C. over 60 minutes while the vacuum is held constant. The shelf temperature is held at −25° C. for about 48 hours. The shelf temperature is then ramped to −10° C. over 60 minutes, and then maintained at −10° C. for 24 hours. Finally, the shelf temperature is ramped to about 35° C. over 60 minutes and then kept at that temperature for about 24 hours. At this point, the chamber is filled with nitrogen to a pressure of about 650 mm Hg and the vials are mechanically stoppered. This procedure results in thermally-stable, vacuum-dried single dose vials containing approximately 500 mg of amifostine (anhydrous basis) and 62.5 mg nicotinamide stabilizer as an elegant cake.

Dosage forms prepared according to this procedure were placed on stability tests, and yielded the results provided in Table 1 below.

5.2. Example 2

Stable Amorphous Amifostine Dosage Form Comprising Nicotinamide and PVP

An aqueous solution of 100 mg/mL amifostine, 12.5 mg/mL nicotinamide (Aldrich), and 10 mg/mL polyvinylpyrrolidone 30 (PVP30: BASF Aktiengesellschaft, Feinchemie, 0-6700 Ludwigshafen, Germany) is sterile filtered at 25° C. through a 0.2 μm filter, and then divided into 5 mL aliquots, each of which is transferred to 10 mL vials. Lyophilization stoppers are placed on the vials and the samples are loaded onto the freeze-dryer shelf maintained at 5° C. The shelf temperature is decreased to −45° C. over 60 minutes, at which temperature it is kept for about 3 hours. The freeze-dryer condenser is then turned on and chamber is evacuated to about 100 μm Hg. After the chamber vacuum has equilibrated, the shelf temperature is ramped to −25° C. over 60 minutes while the vacuum is held constant. The shelf temperature is held at −25° C. for about 12 hours. The shelf temperature is then ramped to −10° C. over 60 minutes, and then maintained at −10° C. for 12 hours. Finally, the shelf temperature is ramped to about 35° C. over 60 minutes and then kept at that temperature for about 6 hours. At this point, the chamber is filled with nitrogen to a pressure of about 650 mm Hg and the vials are mechanically stoppered. This procedure results in thermally-stable, vacuum-dried single dose vials containing approximately 500 mg of amifostine (anhydrous basis), 62.5 mg nicotinamide and 50 mg PVP30 as an elegant cake.

Dosage forms prepared according to this procedure were placed on stability tests, and yielded the results provided in Table 4 below.

5.3. Example 3

Determination of Crystallinity

The crystallinity of the dosage forms of this invention may be determined by powder x-ray diffraction as described, for example, in *Remington's Pharmaceutical Sciences*, 18$^{th}$ ed. page 173; *The United States Pharmacopeia*, 23$^{rd}$ ed. (1995) pages 1843-1844.

FIG. 2 shows a typical powder x-ray diffraction spectrum of a dosage form of amorphous amifostine prepared according to the method of Example 1 which was measured with a Geiger-Müller detector using nickel-filtered Cu Kα radiation. This diffraction pattern contains the broad baseline characteristic of amorphous material. The peaks at 2θ≈14.8, 25.6, and 26.3 are attributed to nicotinamide and/or noise. This assignment is clear from FIG. 3, which shows the x-ray powder diffraction pattern of crystalline nicotinamide.

FIG. 4 shows the difference between the x-ray diffraction patterns of crystalline amifostine prepared as described by U.S. Pat. No. 5,591,731 and that of an amorphous amifostine dosage form of the present invention wherein nicotinamide is used as a stabilizer (8:1 amifostine to nicotinamide weight ratio).

5.4. Example 4

Preferred Manner of Conducting Stability Test of Stable Amorphous Amifostine Dosage Forms The stability of sterile amorphous amifostine dosage forms obtained as described in Example 1 was tested at 5° C. and 25° C. Samples were stored in sealed, nitrogen-filled 10 mL tubing vials.

Results of these tests may be correlated to stability at other temperatures by conventional methods. See, e.g., L. Lachman, et al., *The Theory and Practice of Industrial Pharmacy* pages 766-67 (1986), for a general discussion of stability prediction. From the results of the tests conducted here, decomposition of a dosage form kept at 25° C. for one month is generally equal to about one-half the decomposition of the same dosage form kept at 5° C. for two years.

At the end of each testing period, the amorphous amifostine in the vials was tested for water content, thiol content, and/or amifostine content. In some cases, the water content was determined by Karl Fischer titration. Because amifostine may undergo hydrolysis under stress to produce 2-[(3-aminopropyl)amino]ethane thiol ("WR-1065") and phosphoric acid, determination of the amount of this thiol gives an indication of the stability of the amifostine. Measurement of the amount of amifostine, however, is not preferred, as it has been found that stabilizers such as nicotinamide interfere with assays that determine the amount of amifostine in a sample. Consequently, it is preferred that the decomposition of a sample be determined by analysis of decomposition products, and WR-1065 in particular. Analysis of thiol content was conducted by high pressure liquid chromatography (HPLC) using the following procedure:

1. Preparation of Standards and Samples

Weight and volumes may be adjusted provided the final concentrations remain the same. Store solutions under refrigeration and/or in a refrigerated autosampler immediately after preparation. Shelf-life: 24 hours.

1.1 Preparation of Amifostine Standard Solution

Accurately weigh approximately 30.0 mg of amifostine standarded into a 10-mL volumetric flask. Dissolve in 5 mL of water and dilute to volume with methanol.

1.2 Preparation of 2-[(3-amino propyl)amino]ethanethiol, dihydrochloride (WR-1065) Standard Solution Accurately weigh approximately 7 mg of WR-1065 standard into a 100-mL volumetric flask. Dissolve and dilute to volume with mobile phase.

1.3 Preparation of Amifostine (Drug Substance) for Amifostine Content

Accurately weigh approximately 30.0 mg of amifostine into a 10-mL volumetric flask. Dissolve in 5 mL of water and dilute to volume with methanol.

1.4 Preparation of Amifostine (Drug Substance) for Related Substances

Accurately weigh approximately 150.0 mg of amifostine into a 10-mL volumetric flask. Dissolve and dilute to volume with water.

1.5 Preparation of Amifostine for Injection

Dissolve contents of one drug product vial with about 9 mL water. Quantitatively transfer sample to 50 mL volumetric flask and dilute to volume with water. Transfer 6 mL of this solution to a 25-mL volumetric flask, add 6.5 mL of water and dilute to volume with methanol.

2. System Suitability (Using Standard Solutions)

| Amifostine (Use Standard Solution 1.1) | |
| --- | --- |
| % RSD of 6 Replicate Injection of Amifostine | ≦2% |
| Tailing Factor | ≦2 |
| Theoretical Plates | ≧1,000 |
| WR-1065 (Use Standard Solution 1.2) | |
| % RSD of 6 Injections | ≦4 |
| Tailing Factor | ≦2 |
| Theoretical Plates | ≧7,000 |

3. Equipment and Materials (as Stated Below or Equivalent)

Equipment: HPLC System with UV Detector.

Materials: Amifostine Standard; WR-1065 Standard; Concentrated Phosphoric Acid ($H_3PO_4$) (HPLC Grade); Methanol (MeOH) (HPLC Grade); Purified Water (16 meg-ohm or greater); and 1-Octanesulfonic Acid, Sodium Salt (OSA) (HPLC Grade).

HPLC Chromatrographic Conditions

Column Specifications:

Packing Material: Beckman Ultrasphere ODS (USP L1)

Dimensions: 4.6×250 mm

Particle Size: 5 μm

Mobile Phase: Methanol/Aqueous Phosphoric Acid, pH 2.5, 5 mM OSA (50/50)

1. Dissolve 0.54 g OSA in 500 mL of water, adjust with phosphoric acid to pH 2.5.
2. Dilute to 1000 mL with methanol.
3. Filter and degas the mobile phase.

Detection: 220 nm Absorbance

Flow Rate: 1.0 mL/min

Injection Volume: 10 μL

Column Temperature: Ambient

Sample Temperature: 4° C.

4. Procedure

Inject sample and standard solutions, record retention time of the amifostine peak (approximately 4 minutes). Retention time of the standard amifostine peak and the sample preparation peak should agree within 10% to confirm identification of amifostine in the sample.

5. Calculations

The calculations used to determine the degree of sample decomposition are the same as those described in U.S. Pat. No. 5,591,731, which is hereby incorporated by reference.

5.5. Example 5

Stability Results of Amorphous Amifostine II

Typical results obtained by testing dosage forms of the invention using the method described in Example 4 are summarized below. The dosage form for which data is provided in Table 1 was made by the process described in Example 1. As examination of this data makes clear, the stability of the dosage forms of the present invention is surprisingly independent of their moisture content.

TABLE 1

| Temperature[‡] (° C.) | Time on Stability (days) | % WR-1065 | Moisture Content (%) |
| --- | --- | --- | --- |
| 5 | 20 | 1.32 | 0.52 |
| 5 | 20 | 1.43 | 0.50 |
| 25 | 20 | 3.02 | 0.75 |
| 25 | 20 | 3.07 | 0.86 |
| 25 | 97 | 5.73 | n.d. |
| 25 | 97 | 5.94 | n.d. |

[‡]Temperatures approximately accurate to ±3° C.
n.d. = not determined.

It has been observed that the stability of the dosage forms of this invention can be varied by changing the length of the drying steps, described in Example 1. For example, when vials prepared according to Example 1 are kept at −25° C. for 12 hours, then maintained at −10° C. for 12 hours and finally kept at 35° C. for 6 hours, samples are produced that show the stability results provided in Table 2.

TABLE 2

| Temperature[‡] (° C.) | Time on Stability (days) | % WR-1065 | Moisture Content (%) |
|---|---|---|---|
| 25 | 27 | 3.68 | n.d. |
| 40 | 27 | 21.51 | n.d. |
| 40 | 27 | 14.76 | n.d. |
| 5 | 56 | 0.97 | n.d. |
| 5 | 56 | 1.03 | n.d. |
| 25 | 56 | 5.41 | n.d. |
| 25 | 56 | 5.28 | n.d. |
| 5 | 91 | 0.96 | 5.13 |
| 5 | 91 | 1.12 | 4.35 |
| 25 | 91 | 7.03 | 4.57 |
| 25 | 91 | 6.73 | 3.6 |

[‡]Temperatures approximately accurate to ±3° C.
n.d. = not determined.

The above results clearly indicate the enhanced thermal-stability of the amifostine dosage form produced by the method described herein. The enhanced stability is evident from the low weight percent of thiol formation, which indicates very little decomposition of the amifostine to form 2-[(3-aminopropyl)amino]ethane thiol (WR-1065).

The exceptional and unexpected thermal stability of the dosage forms of this invention is also apparent from Table 3, which provides stability measurements of conventional dosage forms of amifostine (Amorphous Amifostine I), dosage forms of this invention (Amorphous Amifostine II), and the crystalline dosage form of U.S. Pat. No. 5,424,471 ("Crystalline Ethyol®"). It is clear that the dosage form of the present invention possesses stability heretofore only exhibited by crystalline dosage forms.

TABLE 3

| Dosage Form | % Water | 1 Month 40° C.[‡] | 3 Months 25° C.[‡] | 3 Months 25° C.[‡] | 2 Years 5° C.[‡] |
|---|---|---|---|---|---|
| Amorphous Amifostine I[a] | ~6% | n.d. | 6.0 | 13.8 | 3.5 |
| Amorphous Amifostine II[b] | ~1% | 18.1 | 3.0[f] | 5.8 | n.d. |
| Amorphous Amifostine II[c] | ~5% | n.d. | 3.7 | 6.9 | n.d. |
| Amorphous Amifostine II[d] | ~6% | n.d. | 5.0 | n.d. | n.d. |
| Amorphous Amifostine II[e] | ~6% | n.d. | 3.3 | n.d. | n.d. |
| Crystalline Ethyol ® | ~20% | 0.6 | n.d. | 0.4 | 0.5 |

[a]Comprising mannitol as an excipient in a 1:1 ratio.
[b]Comprising nicotinamide as a stabilizer in a 8:1 ratio (amifostine to nicotinamide).
[c]Comprising nicotinamide as a stabilizer in a 8:1 ratio (amifostine to nicotinamide).
[d]Comprising nicotinamide as a stabilizer in a 8:1 ratio (amifostine to nicotinamide).
[e]Dosage form produced by the methods of this invention comprising nicotinamide as a stabilizer in a 4:1 ratio (amifostine to nicotinamide) (a mixture of crystalline and amorphous).
[f]Duration of 20 days.
[‡]Temperatures approximately accurate to ±3° C.
n.d. = not determined.

Further, as can be seen from Table 3, variations in drying cycle can affect thermal-stability. For example, Amorphous Amifostine I was prepared using the prior method discussed above, while the embodiments of Amorphous Amifostine II were prepared using different drying cycles. Using the superscripts of Table 3, Amorphous Amifostine II[b] was prepared using the drying cycle of Example 1, and Amorphous Amifostine II[c] was prepared using the drying cycle described above that provided the results in Table II. Amorphous Amifostine II[d] and Amorphous Amifostine II[e] were both prepared using the following drying cycle: freezing for about 3 hours at a temperature of about −45° C.; primary drying for about 60 hours at a temperature of about −25° C.; and secondary drying for about 24 hours at about −10° C., and then for about 6 hours at about 0° C.

Dosage forms comprising amifostine, nicotinamide, and an excipient also exhibit surprising stability. For example, dosage forms prepared according to the method of Example 2, wherein the excipient is PVP30, provide the stability data shown in Table 4.

TABLE 4

| Temperature[‡] (° C.) | Time on Stability (days) | % WR-1065 | Moisture Content (%) |
|---|---|---|---|
| 5 | 45 | 0.66 | 5.15 |
| 25 | 45 | 1.96 | n.d. |
| 5 | 110 | 0.84 | n.d. |
| 25 | 110 | 2.40 | n.d. |

[‡]Temperatures approximately accurate to ±3° C.
n.d. = not determined.

Amifostine compositions of the invention that simply comprise amifostine and an excipient provide the stability data shown in Table 5. These compositions were prepared using the lyophilization cycle described in Example 2.

TABLE 5

| Excipient | Temperature[‡] (° C.) | Time on Stability (days) | % WR-1065 | Moisture Content (%) |
|---|---|---|---|---|
| PVP30[a] | 5 | 45 | 1.26 | 3.26 |
| sucrose[b] | 5 | 45 | 0.78 | 4.95 |
| CMC[c] | 5 | 45 | 0.93 | 3.84 |
| dextran[d] | 5 | 45 | 1.01 | 3.87 |
| PVP30[a] | 25 | 45 | 4.80 | n.d. |
| sucrose[b] | 25 | 45 | 4.29 | n.d. |
| CMC[c] | 25 | 45 | 4.21 | n.d. |
| dextran[d] | 25 | 45 | 5.10 | n.d. |
| PVP30[a] | 5 | 110 | 1.57 | n.d. |
| sucrose[b] | 5 | 110 | 1.55 | n.d. |
| CMC[c] | 5 | 110 | 1.26 | n.d. |
| dextran[d] | 5 | 110 | 1.37 | n.d. |

[‡]Temperatures approximately accurate to ±3° C.
[a]Comprising PVP30 in a ratio of 10:1 (amifostine to PVP30).
[b]Comprising sucrose in a ratio of 10:1 (amifostine to sucrose).
[c]Comprising low viscosity carboxymethyl cellulose sodium salt (CMC) in a ratio of 40:1 (amifostine to CMC).
[d]Comprising dextran in a ratio of 10:1 (amifostine to dextran).
n.d. = not determined.

From these results, it is clear that the amorphous amifostine of the invention can be combined with a wide variety of excipients to yield thermally stable amorphous amifostine compositions.

It should be apparent to one of ordinary skill that other embodiments not specifically disclosed nonetheless fall within the scope and spirit of the present invention. Hence, the descriptions herein should not be taken as limiting the invention in any way, except as stated in the following claims.

What is claimed is:

1. A method for protecting against the adverse effects which arise during the use of chemotherapy or radiation therapy in the treatment of cancer comprising administering to a subject an amorphous a dosage form of amifostine which comprises sterile, amorphous amifostine which is suitable for reconstitution with a pharmaceutically-acceptable vehicle into an injectable particulate-free drug product for parental administration to a subject, wherein said amorphous amifostine forms:
(a) less than about 5 weight percent of 2-[(3aminopropyl)amino]ethane thiol when maintained at a temperature of about 40° C. for about one week;
(b) less than about 5 weight percent of 2-[(3aminopropyl)amino]ethane thiol when maintained at a temperature of about 25° C. for about one month; or
(c) less than about 3 weight percent of 2-[(3aminopropyl)amino]ethane thiol when maintained at a temperature of about 5° C. for about two years;
thereby protecting against the adverse effects which arise during the use of chemotherapy or radiation therapy in the treatment of cancer.

2. The method of claim 1, further comprising a stabilizer.

3. The method of claim 2, wherein the molar ratio of stabilizer to amifostine is between 0.05 and 5.0.

4. The method of claim 3, wherein the stabilizer is an amide or an amino acid.

5. The method of claim 4, wherein the amide or amino acid is selected from the group consisting of nicotinamide, derivatives of nicotinamide, nicotinic acid, derivatives of nicotinic acid, glycine, alanine, valine, leucine, isoleucine, phenylalanine, trytophan, asparagines, and mixtures thereof.

6. The method of claim 4, wherein said stabilizer is nicotinamide, used in an amifostine to nicotinamide weight ratio of between 4:1 and 10:1.

7. The method of claim 6, wherein the amifostine to nicotinamide weight ratio is about 8:1.

8. The method of claim 1 further comprising an excipient.

9. The method of claim 8, wherein the excipient is selected from the group consisting of sodium chloride, citric acid, tartaric acid, gelatin, polyvinylpyrrolidone, diethylenetriamine-pentaacetic acid, ethylenediamine-tetraacetic acid, sodium deoxycholate, sodium taurocholate, dextrose, sucrose, sorbitol, inositol, dextran, mannitol, carboxymethyl cellulose sodium salt, and mixture thereof.

10. The method of claim 1, wherein said dosage form has a water content of up to about 20 weight percent.

11. The method of claim 1, wherein said dosage form is at least about 80% amorphous by weight.

* * * * *